United States Patent
Voss et al.

[11] Patent Number: 5,848,970
[45] Date of Patent: Dec. 15, 1998

[54] APPARATUS AND METHOD FOR NON-INVASIVELY MONITORING A SUBJECT'S ARTERIAL BLOOD PRESSURE

[75] Inventors: Gregory I. Voss, Solana Beach; Alvis J. Somerville, San Diego, both of Calif.

[73] Assignee: VitalWave Corp., San Diego, Calif.

[21] Appl. No.: 766,810

[22] Filed: Dec. 13, 1996

[51] Int. Cl.[6] .................................................. A61B 5/00
[52] U.S. Cl. .......................................... 600/485; 600/500
[58] Field of Search ........................... 600/485, 500–503, 600/561

[56] References Cited

U.S. PATENT DOCUMENTS

| | | | |
|---|---|---|---|
| 4,651,747 | 3/1987 | Link | 128/677 |
| 4,771,792 | 9/1988 | Seale . | |
| 4,869,261 | 9/1989 | Penaz | 128/667 |
| 4,901,733 | 2/1990 | Kaida et al. | 600/485 |
| 4,924,871 | 5/1990 | Honeyager . | |
| 5,119,822 | 6/1992 | Niwa | 600/503 |
| 5,240,007 | 8/1993 | Pytel et al. . | |
| 5,439,001 | 8/1995 | Butterfield et al. | 128/672 |
| 5,450,852 | 9/1995 | Archibald et al. | 128/672 |
| 5,467,771 | 11/1995 | Narimatsu et al. | 128/672 |
| 5,494,043 | 2/1996 | O'Sullivan | 600/500 |
| 5,634,467 | 6/1997 | Nevo . | |
| 5,649,542 | 7/1997 | Archibald et al. . | |

FOREIGN PATENT DOCUMENTS

| | | | |
|---|---|---|---|
| 284095 | 9/1988 | European Pat. Off. | A61B 5/02 |
| WO 84/00290 | 2/1984 | WIPO | A61B 5/02 |
| WO95/13014 | 5/1995 | WIPO | A61B 5/021 |

*Primary Examiner*—Robert L. Nasser
*Attorney, Agent, or Firm*—Sheppard, Mullin, Richter & Hampton LLP; James R. Brueggemann

[57] ABSTRACT

Apparatus is disclosed for non-invasively monitoring a subject's blood pressure, in which a flexible diaphragm that encloses a fluid-filled chamber is compressed against tissue overlying an artery, with sufficient force to compress the artery. A first, relatively slow servo control system optimizes the amount of artery compression, which occurs at a mean transmural pressure of about zero, by modulating the volume of fluid within the chamber and noting the resulting effect on the pressure within the chamber. Since different pressure effects are realized according to the amount of artery compression, an appropriate control signal can be produced that provides the optimum mean diaphragm pressure. In addition, a second, relatively fast servo control system supplies the fluid to and from the chamber, so as to compensate for pressure variations within artery. This minimizes variations in the artery's effective diameter, whereby the pressure within the fluid-filled chamber closely follows the actual arterial pulse waveform.

43 Claims, 8 Drawing Sheets

APPARATUS AND METHOD FOR NON-INVASIVELY MONITORING A SUBJECT'S ARTERIAL BLOOD PRESSURE

BACKGROUND OF THE INVENTION

This invention relates generally to apparatus and methods for monitoring a subject's arterial blood pressure and, more particularly, to such apparatus and methods that monitor arterial blood pressure non-invasively by applying a pressure sensor against tissue overlying an arterial blood vessel, to partially applanate or compress the vessel.

Two well known techniques have been used to non-invasively monitor a subject's arterial blood pressure waveform, namely, auscultation and oscillometry. Both techniques use a standard inflatable arm cuff that occludes the subject's brachial artery. The auscultatory technique determines the subject's systolic and diastolic pressures by monitoring certain Korotkoff sounds that occur as the cuff is slowly deflated. The oscillometric technique, on the other hand, determines these pressures, as well as the subject's mean pressure, by measuring actual pressure changes that occur in the cuff as the cuff is deflated. Both techniques determine pressure values only intermittently, because of the need to alternately inflate and deflate the cuff, and they cannot replicate the subject's actual blood pressure waveform. Thus, true continuous, beat-to-beat blood pressure monitoring cannot be achieved using these techniques.

Occlusive cuff instruments of the kind described briefly above generally have been effective in sensing long-term trends in a subject's blood pressure. However, such instruments generally have been ineffective in sensing short-term blood pressure variations, which are of critical importance in many medical applications, including surgery.

One technique that has been used to provide information about short-term blood pressure variations is called arterial tonometry. One device for implementing this technique includes a rigid array of miniature pressure transducers that is applied against the tissue overlying a peripheral artery, e.g., the radial artery. The transducers each directly sense the mechanical forces in the underlying subject tissue, and each is sized to cover only a fraction of the underlying artery. The array is urged against the tissue, to applanate the underlying artery and thereby cause beat-to-beat pressure variations within the artery to be coupled through the tissue to the transducers.

The rigid arterial tonometer described briefly above is subject to several drawbacks. First, its discrete transducers are relatively expensive and, because they are exposed, they are easily damaged. In addition, the array of discrete transducers generally is not anatomically compatible with the continuous contours of the subject's tissue overlying the artery being sensed. This has led to inaccuracies in the resulting transducer signals. In addition, in some cases, this incompatibility can cause tissue injury and nerve damage and can restrict blood flow to distal tissue. Another drawback is that such rigid arterial tonometers have failed to correct for signal artifacts that arise when the subject's arm is moved. This is a particular problem when the subject is exercising or otherwise ambulating.

Yet another drawback to the arterial tonometer described briefly above is its inability to continuously monitor and adjust the level of arterial wall compression to an optimum level of zero transmural pressure. Generally, optimization of arterial wall compression has been achieved only by periodic recalibration. This has required an interruption of the patient monitoring function, which sometimes can occur during critical periods. This drawback is perhaps the most severe factor limiting acceptance of tonometers in the clinical environment.

Another device functioning similarly to the arterial tonometer includes a housing having a closed, liquid-filled chamber with one wall of the chamber defined by a flexible diaphragm. The device is applied against a subject's skin, with the flexible diaphragm pressed against the tissue overlying a peripheral artery, e.g., the radial artery, and several electrodes located in separate compartments of the chamber sense volume changes in the compartments that result from the beat-to-beat pressure variations in the underlying artery. Although the device seeks to replicate the arterial pressure waveform, it is considered to have a relatively low gain, making it unduly susceptible to noise. Further, the device must be calibrated periodically, during which time its continuous monitoring of the subject's blood pressure waveform necessarily is interrupted.

It should, therefore, be appreciated that there is a continuing need for an apparatus, and related method, for non-invasively and continuously monitoring a subject's blood pressure, with reduced susceptibility to noise and without the need to intermittently interrupt the device's normal operation for calibration. The present invention fulfills this need.

SUMMARY OF THE INVENTION

The present invention resides in an improved apparatus, and related method, for non-invasively monitoring a subject's arterial blood pressure, with reduced susceptibility to noise and without the need to intermittently interrupt the pressure monitoring for calibration. The apparatus includes a pressure sensor assembly that produces a pressure signal indicative of the pressure applied against it and further includes a coupling device that urges the pressure sensor assembly into compressive engagement with tissue overlying the subject's blood vessel, to compress the vessel and ensure that pressure variations within the vessel are coupled through the tissue to the assembly. A controller controllably modulates the position of the pressure sensor assembly relative to the subject's blood vessel and monitors the resulting effect on the pressure signal, to produce a control signal that controllably positions the pressure assembly relative to the subject's blood vessel such that the vessel is compressed by a prescribed mean amount. This optimizes the coupling between the blood vessel and the sensor assembly. The pressure sensor assembly thereby senses the subject's blood pressure in an optimal manner.

More particularly, in one form of the invention, the pressure sensor assembly includes a base having an open cavity, with a flexible diaphragm extending across the cavity to define a closed, fluid-filled chamber. The controller is a fluid volume controller configured to controllably supply a fluid to and from the closed chamber, to vary the position of the flexible diaphragm relative to the tissue overlying the subject's blood vessel. By monitoring the resulting effect on the pressure signal, the controller can supply an amount of fluid to the chamber such that the subject's blood vessel is compressed by the prescribed mean amount.

In a separate and independent feature of the invention, the fluid volume controller is configured to controllably supply fluid to and from the closed chamber so as to substantially balance the variable force applied to the diaphragm by any pressure variations in the patient's blood vessel. This enables the vessel to assume an optimal geometry continuously, even during short term pressure variations due, for example, to a heartbeat pulse. This enables the masking effect of the tissue overlying the vessel to be effectively eliminated, and it enables a substantially increased gain and noise immunity to be provided.

An optimal vessel geometry is provided when the vessel's mean transmural pressure is substantially zero. This optimal vessel geometry is achieved by configuring the fluid volume controller to modulate the fluid volume within the closed chamber while monitoring the resulting effect on the pressure signal, to produce a control signal that then is used to regulate the fluid volume such that the diaphragm is maintained at the optimal position.

More particularly, the fluid volume controller includes a vessel geometry sensor that produces a vessel geometry signal indicative of the actual geometry of the subject's blood vessel, an error signal generator that generates an error signal indicative of any difference between the actual geometry of the blood vessel and a prescribed geometry of the vessel, and a summer, responsive to the vessel geometry signal and the error signal, that produces the control signal. A fluid supply supplies the fluid to and from the closed chamber based on this control signal.

The error signal generator can include a diaphragm position sensor, in which case the vessel geometry signal is indicative of the actual position of the flexible diaphragm relative to the base. The diaphragm position sensor can include a signal generator that generates a modulation signal coupled to the summer, for incorporation into the control signal. This modulation signal causes the fluid volume controller to supply the fluid to and from the closed chamber in a manner that modulates the actual position of the flexible diaphragm about a mean position. A analyzer compares the modulation signal with the pressure signal, to sense any deviation of the diaphragm's actual mean position from a prescribed mean position and to produce the error signal.

In a more detailed feature of the invention, which can be implemented whether or not the pressure sensor assembly is coupled by a fluid to the subject's blood vessel, the modulation signal includes a succession of alternating positive and negative lobes of substantially uniform amplitude, e.g., a sine wave, and it has a frequency substantially greater than the subject's expected heartbeat frequency. In one embodiment, the analyzer is configured to compare the effects that the positive and negative lobes of the modulation signal have on the pressure signal, to detect any deviation of the pressure sensor assembly's actual mean position from its prescribed mean position. In an alternative embodiment, the analyzer is configured to compares the ac amplitude of the pressure signal during a first stage of the subject's heartbeat (e.g., systole) with the ac amplitude of the pressure signal during a second stage of the heartbeat (e.g., diastole), to sense any deviation of the assembly's actual mean position from its prescribed mean position.

In another separate and independent feature of the invention, a controller is configured to controllably modulate the position of the pressure sensor assembly relative to the subject's blood vessel with a periodic signal having a frequency substantially greater than the frequency of the subject's expected heartbeat, and the controller monitors the resulting pressure signal to produce a plurality of pressure waveforms. Each such pressure waveform corresponds to a different phase of the periodic signal, which in turn corresponds to a different nominal amount of vessel compression. The controller is configured to select the particular one of the pressure waveforms that derives from a transmural pressure of substantially zero, for example by selecting the particular waveform for which the pressure signal at systole differs from the pressure signal at diastole by a maximum amount.

Other features and advantages of the present invention should become apparent from the following description of the preferred embodiments, taken in conjunction with the accompanying drawings, which illustrate, by way of example, the principles of the invention.

DESCRIPTION OF THE PREFERRED EMBODIMENTS

Figure 1:
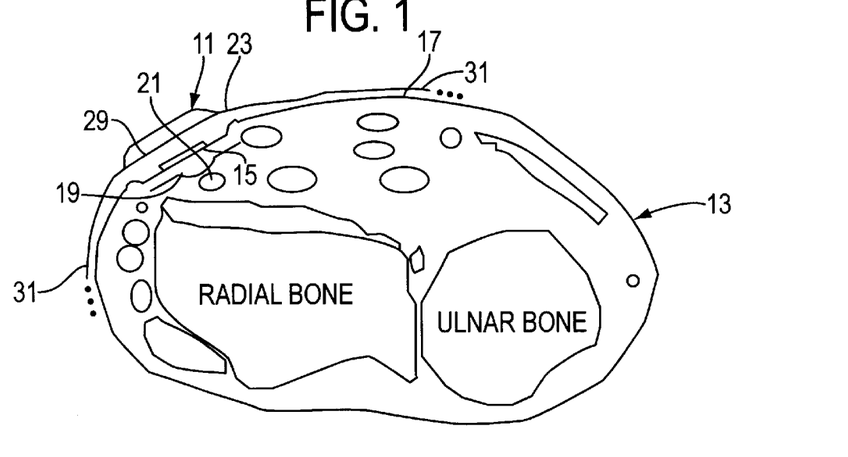
FIG. 1 is a schematic cross-sectional view of a pressure sensor assembly in accordance with the invention, in its prescribed position secured to a subject's wrist, with a flexible diaphragm and liquid-filled chamber disposed adjacent to the subject's radial artery.
Figure 2:
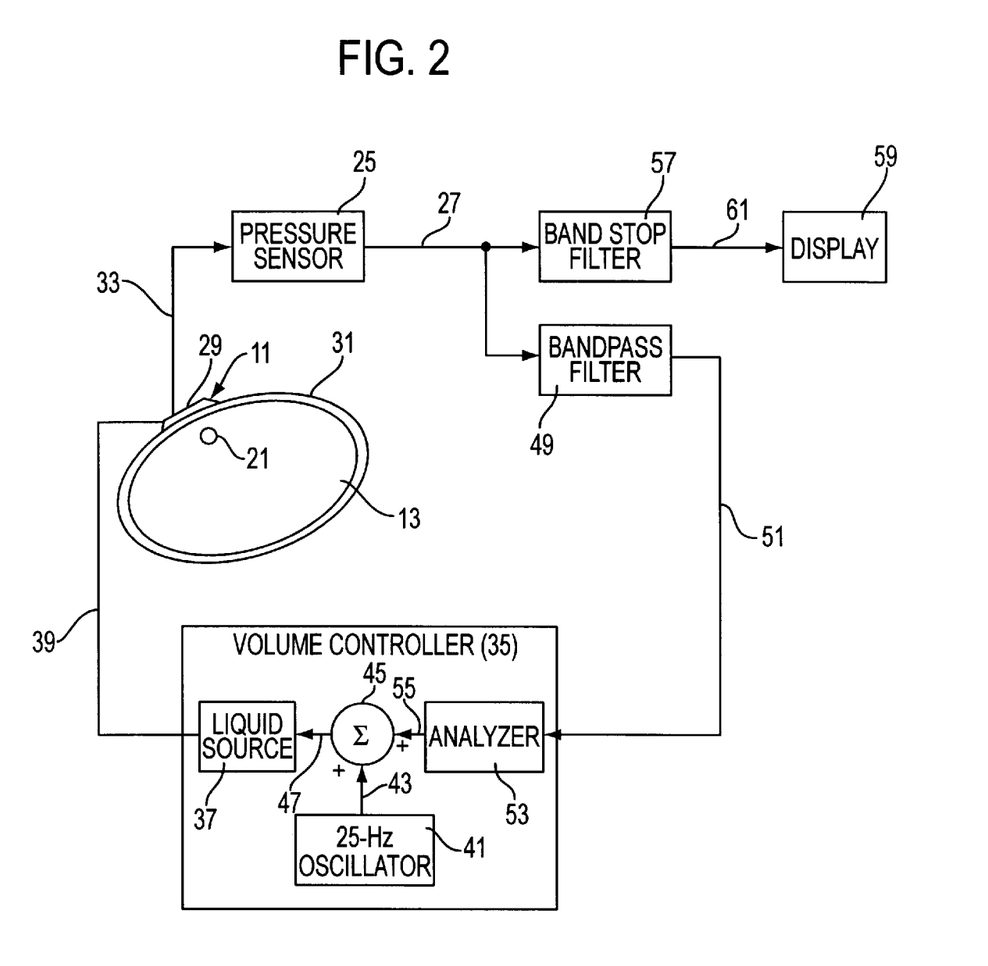
FIG. 2 is a block diagram of a first embodiment of a blood pressure monitoring apparatus in accordance with the invention, incorporating the pressure sensor assembly of FIG. 1.

With reference now to the drawings, and particularly to FIGS. 1 and 2, there is shown a blood pressure monitoring apparatus having a sensor assembly 11 configured for attachment to a subject's wrist 13, with a flexible diaphragm 15 of the assembly compressively engaging the skin 17 and other tissue 19 overlying the subject's radial artery 21. Blood pressure variations within the artery are coupled through the tissue to the diaphragm, and through a liquid-filled chamber 23 located behind the diaphragm, to a pressure sensor 25, to produce a pressure signal output on line 27 that represents the artery's pressure waveform.

More particularly, the sensor assembly 11 includes a plastic base 29 having the shape of an inverted, shallow cup, and a wrist strap 31 that holds the base in its prescribed position on the subject's wrist 13. The flexible diaphragm 15 extends across the opening of the cup-shaped base, to define the chamber 23 that carries a suitable working liquid, e.g., water. When the sensor assembly is properly secured to the subject's wrist, it compressively engages the skin 17 and adjacent tissue 19 and compresses the radial artery 21. The amount of compression affects the degree of coupling of the pressure variations within the artery to the liquid-filled chamber 23 and, in turn, to the pressure sensor 25. The pressure sensor is coupled to the liquid-filled chamber via a low-compliance conduit 33.

Figure 3:
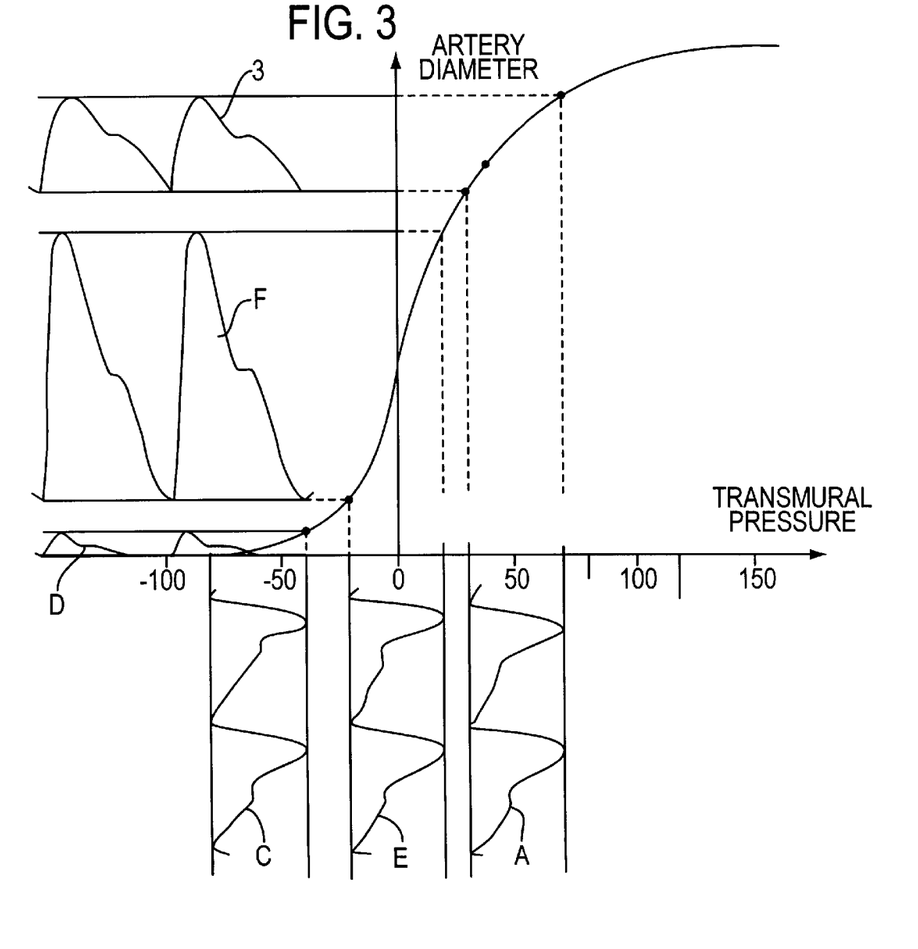
FIG. 3 is a graph depicting the typical sigmoid relationship between the transmural pressure of a subject's radial artery and the artery's effective diameter. Superimposed on the graph are several waveforms representing the subject's actual blood pressure over several heartbeats, along with waveforms representing the resulting changes in the artery's effective diameter for conditions of under compression, optimal compression, and over compression.

FIG. 3 is a graph depicting the sigmoidal relationship between the radial artery's transmural pressure and the artery's volume, or effective diameter. Transmural pressure is the pressure across the artery wall, i.e., the pressure inside the artery minus the pressure outside the artery. A high transmural pressure indicates that the artery 21 is compressed by a small amount and thus has a relatively large effective diameter, whereas a low transmural pressure indicates that the artery is compressed by a large amount, i.e., has a flattened, oval shape and thus has a relatively small effective diameter.

It will be noted in FIG. 3 that a normal arterial pressure variation of about 50 mmHg (i.e., 50 millimeters of mercury), due to a normal heartbeat, will cause the artery's transmural pressure to vary by 50 mmHg, as well. This assumes, of course, that the pressure outside the artery 21 remains unchanged.

When the artery 21 is compressed by only a small amount, i.e., when the mean transmural pressure is highly positive, this 50 mmHg pressure excursion will cause only a relatively small change in the artery's effective diameter. This relationship is shown by the vertically oriented waveform identified by the reference letter A in FIG. 3 and the horizontally oriented waveform identified by the reference letter B. Similarly, when the artery is compressed by a large amount, i.e., when the mean transmural pressure is highly negative, this 50 mmHg pressure excursion likewise will cause only a relatively small change in the artery's effective diameter. This relationship is shown by the vertically oriented waveform identified by the reference letter C and the horizontally oriented waveform identified by the reference letter D.

However, if the artery 21 is compressed by an amount that corresponds to a mean transmural pressure near zero, this 50 mmHg pressure excursion will cause a relatively large change in the artery's effective diameter. This relationship, which is shown by the waveforms identified by the reference letters E and F in FIG. 3, represents a maximum coupling between the arterial pressure and the sensor assembly 11.

When the artery has this geometry, the arterial wall is unable to carry stress loads. It is desirable, therefore, to regulate the mean arterial compression to match this optimum value.

To this end, the apparatus further includes a volume controller 35 having a liquid source 37 that supplies liquid to and from the chamber 23 of the sensor assembly 11, via a conduit 39. The volume controller implements a control scheme that regulates the volume of liquid within the chamber so as to provide optimal compression of the subject's radial artery 21. Under this control scheme, the volume controller actively varies the position of the sensor assembly's flexible diaphragm 15, so as to modulate, or dither, the effective diameter of the subject's artery 21, and it analyzes the resulting effect on the pressure signal produced by the pressure sensor 25. Different effects on the pressure signal are provided according to the amount of artery compression.

The volume controller 35 effects this modulation of the diaphragm's position by applying a 25-Hz sinusoidal signal to the liquid source 37. This sinusoidal signal is produced by an oscillator 41 and coupled via line 43 to a summer 45 and, in turn, via line 47 to the liquid source. A 25-Hz frequency is selected, because it is generally higher than the highest frequency components of interest in the artery's blood pressure waveform.

Figure 4A:
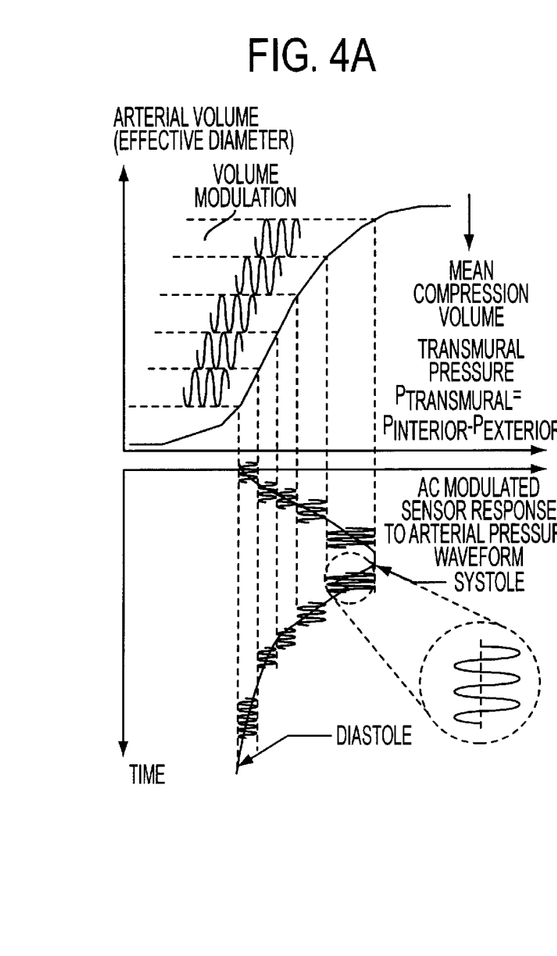
FIGS. 4A–4C are graphs depicting the sigmoid curve of FIG. 3 and showing the effects of a small volume modulation on the transmural pressure over the time period of one heartbeat, for conditions of under compression, over compression, and optimal compression, respectively.
Figure 5A:
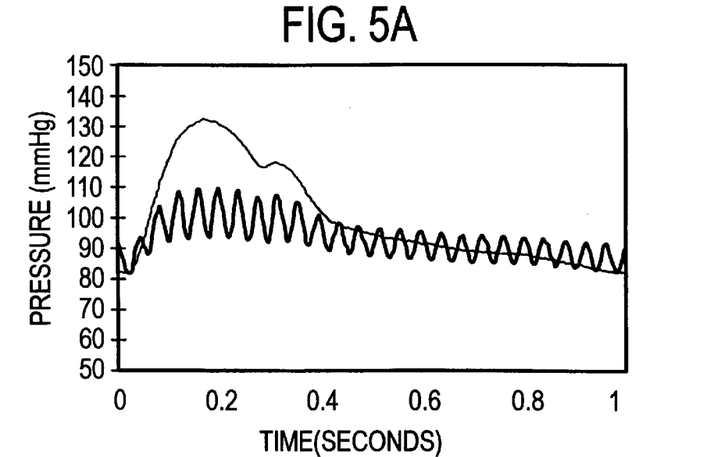
FIGS. 5A–5C are graphs of typical pressure signal waveforms over one heartbeat that are provided by the blood pressure monitoring apparatus of FIG. 2, for conditions of under compression, over compression, and optimal compression, respectively. The waveforms incorporate pressure oscillations that result from application of a 25-Hz modulation of the volume in the liquid-filled chamber.

It will be appreciated that, if the artery 21 is under compressed, then the ac pressure response to the 25-Hz volume oscillation will be larger during systole than during diastole. This is because an incremental arterial volume change (i.e., an incremental vertical movement along the sigmoid curve of FIG. 3) will induce a greater pressure change (i.e., horizontal movement along the curve of FIG. 3) when the pressure is highest, i.e., at systole, than when the pressure is lowest, i.e., at diastole. This phenomenon is depicted in FIG. 4A, and also in FIG. 5A, which shows the pressure signal on line 27 aligned with the pressure waveform representing one heartbeat, including both a systolic stage and a diastolic stage. It will be noted that the pressure signal's ac amplitude is substantially greater during the systolic stage than during the diastolic stage.

Figure 4B:
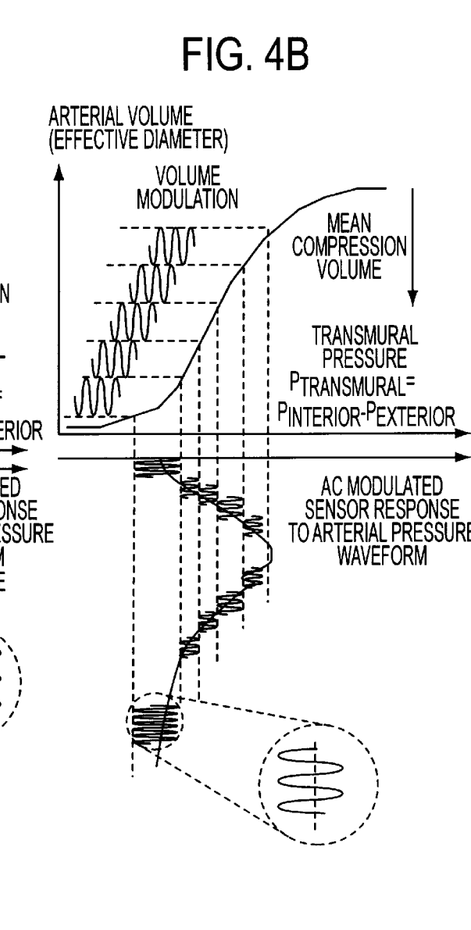
Figure 5B:
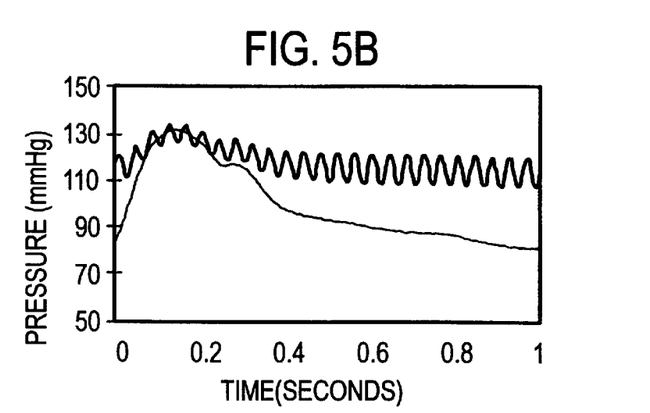

Conversely, if the artery 21 is over compressed, then the ac amplitude of the 25-Hz pressure oscillation will be larger during diastole than during systole. This is because an incremental change in the effective diameter of the artery (i.e., an incremental vertical movement along the curve of FIG. 3) will induce a greater pressure change (i.e., horizontal movement along the curve of FIG. 3) when the pressure is lowest, i.e., at diastole, than when the pressure is highest, i.e., at systole. This phenomenon is depicted in FIG. 4B, and also in FIG. 5B, which shows the pressure signal on line 27 aligned with the pressure waveform representing one heartbeat. It will be noted that the pressure signal ac amplitude is substantially greater during the diastolic stage than during the systolic stage.

Figure 4C:
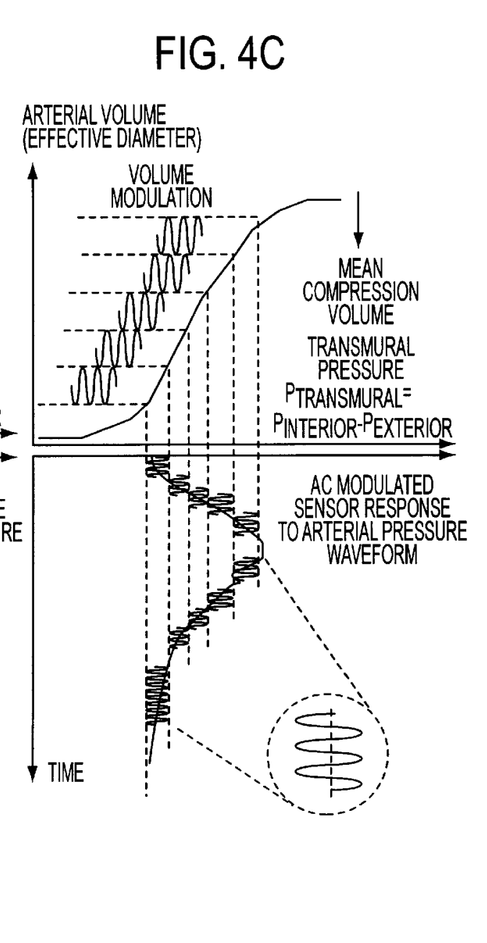
Figure 5C:
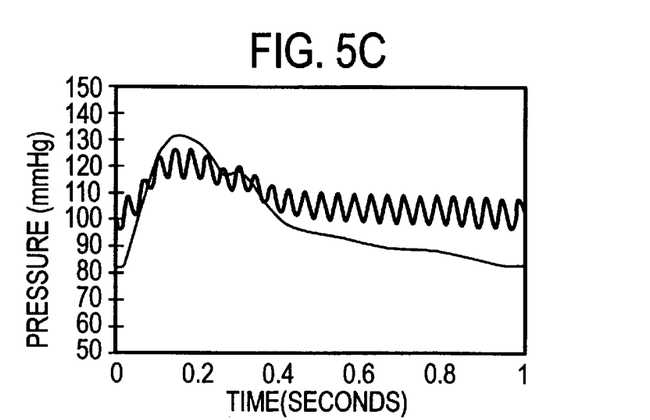

However, if the artery 21 is optimally compressed, then the ac amplitudes of the 25-Hz pressure oscillation during the systolic and end-diastolic stages will be substantially the same. In addition, the overall amplitude of the pressure oscillation is at a minimum when the artery is optimally compressed. This is because the sigmoid curve of FIG. 3 is steepest at the point of optimal compression. These phenomena are depicted in FIG. 4C, and also in FIG. 5C, which shows the pressure signal on line 27 aligned with the pressure waveform representing one heartbeat.

The control system for implementing the control scheme described above is depicted in FIG. 2. In addition to the volume controller 35, the sensor assembly 11, and the pressure sensor 25 identified above, the control system further includes a 25-Hz bandpass filter 49 that filters the pressure signal received on line 27 from the pressure sensor. The filtered signal, which incorporates only the 25-Hz component of the pressure signal, is supplied on line 51 to the volume controller. An analyzer 53 that is part of the volume controller receives the filtered signal and compares its ac amplitude during systole with its ac amplitude during diastole, to determine whether the artery 21 is under compressed, over compressed, or optimally compressed. The analyzer produces a corresponding error signal that is supplied on line 55 to the summer 45, which sums the error signal with the 25-Hz modulation signal, to produce a control signal that controls the liquid source 37.

Operation of the control system automatically regulates the amount of liquid in the liquid-filled chamber 23 of the sensor assembly 11 such that the assembly optimally compresses the subject's radial artery 21. For example, if the analyzer 53 of the volume controller 35 determines that the ac amplitude of the filtered pressure signal is greater during systole than it is during diastole, then a positive error signal is produced, which is coupled through the summer 45 to the liquid source 37, to supply additional liquid to the sensor chamber and thereby increase the compression of the artery. The opposite would occur if the analyzer determines that the filtered pressure signal's ac amplitude is greater during diastole than it is during systole.

To provide a visible display of the subject's arterial pressure waveform, the apparatus further includes a 25-Hz band stop filter 57 and a display 59. The filter receives the pressure signal on line 27 from the pressure sensor 25, and it samples this signal at a rate of 50 samples per second. This sampling is phased with the 25-Hz modulation signal output on line 43 by the oscillator 41 such that it always occurs at the modulation signal's zero crossings. The sampled pressure signal then is coupled on line 61 to the display, for real-time display. The use of a low-compliance liquid within the sensor chamber 23 in contrast with a relatively high-compliance gaseous fluid, provides improved coupling between the artery 21 and the pressure sensor 25.

In an alternative embodiment of the invention, not depicted in the drawings, modulation of a pressure sensor assembly relative to the subject's radial artery is achieved not by fluid volume modulation, but rather by a lever that is connected via an eccentric to a dc motor. Rotation of the motor at a frequency of, say, 25 Hz causes the sensor assembly to move toward and away from the patient's artery correspondingly.

In an independent feature of the invention, enhanced coupling of the pressure variance within the subject's radial artery 21 due to heartbeats is provided by actively maintaining the artery fixed at its optimal compression level throughout each heartbeat pulse. This is accomplished by a second, faster control system, which servo controls, in real time, the amount of liquid in the chamber 23 of the sensor assembly 11 so as to counteract the effect of the arterial pressure variations. Moreover, this servo control is effected in combination with the first, slower control system, which regulates the sensor assembly to provide the optimal mean artery compression, as described above. A block diagram of a blood pressure monitoring apparatus that implements both such control system s is provided in FIG. 6. Major portions of this apparatus are identical to the apparatus of FIG. 2 and are identified by the same reference numerals.

Figure 6:
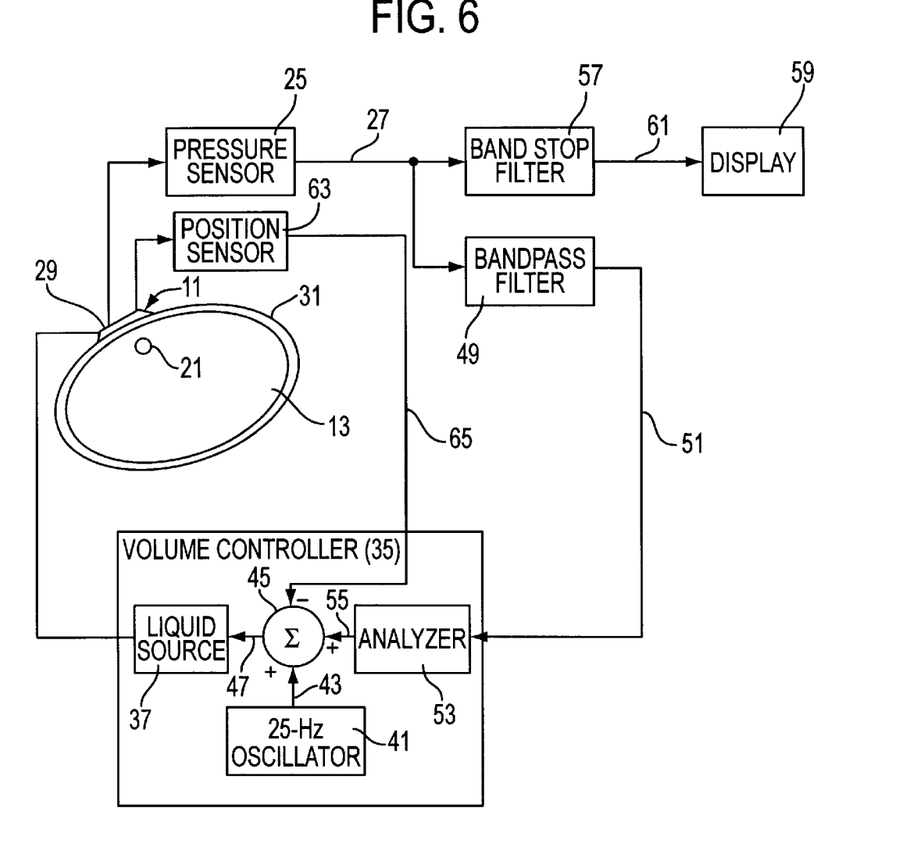
FIG. 6 is a block diagram of a second embodiment of a blood pressure monitoring apparatus in accordance with the invention, incorporating the pressure sensor assembly of FIG. 1.

With reference to FIG. 6, an optical position sensor 63 (e.g., incorporating a light-emitting diode and a photodiode) is carried on the base 29 of the sensor assembly 11, to provide a signal that indicates the position of the flexible diaphragm 15 relative to the base. The diaphragm position can be assumed to be related directly to the position of the subject's skin and, thus, to the effective diameter of the subject's radial artery 21. The position signal is coupled via line 65 from the position sensor directly to the summer 45 of the volume controller 35, for incorporation into the control signal supplied on line 47 to the liquid source 37.

Thus, for example, as the pressure within the artery 21 rises during systole, the position sensor 63 senses an increase in the artery's effective diameter and the position signal therefore exhibits a corresponding increase. This increase is coupled to the liquid source 37, which responds by supplying sufficient additional liquid through the conduit 39 to the chamber 23 of the sensor assembly 11 to counteract the increased pressure. The result is that the artery's effective diameter remains substantially fixed throughout the arterial pulse. A loop bandwidth of about 100 Hz is preferred, which is significantly higher than the 25-Hz modulation signal and the important harmonics of the arterial pulse.

As the liquid source 37 of the volume controller 35 regulates the volume of liquid within the chamber 23 of the sensor assembly 11 so as to maintain the effective diameter of the subject's radial artery 21 substantially fixed, the pressure within the chamber necessarily will vary. This pressure variance within the chamber will closely match the pressure waveform of the artery.

Moreover, this close match between arterial pressure and chamber pressure will occur even if a gas were to be substituted for the liquid within the chamber 23. This is because the fast servo control system provides for a virtual low compliance, even though the fluid itself might have a relatively high compliance. In some applications, the use of a gas (e.g., air) within the chamber is preferred, to simplify certain aspects of the control system's design. When a gas is used, a greater volume will need to be transported to and from the chamber; however, the servo control system can readily accomplish this.

Figure 7A:
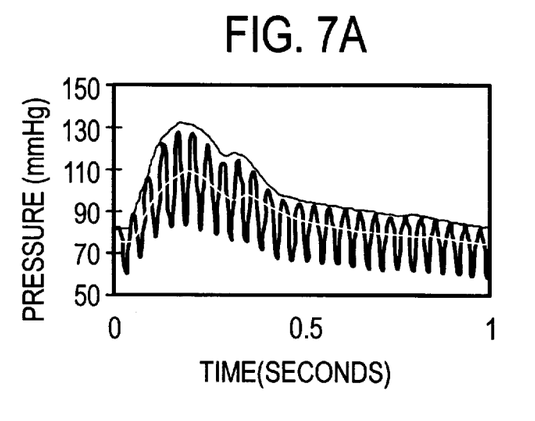
FIGS. 7A–7C are graphs of typical mean transmural pressure signal waveforms over one heartbeat that are provided by the blood pressure monitoring apparatus of FIG. 6, for conditions of under compression, over compression, and optimal compression, respectively. The waveforms incorporate pressure oscillations that result from application of a 25-Hz modulation of the volume in the liquid-filled chamber.
Figure 7B:
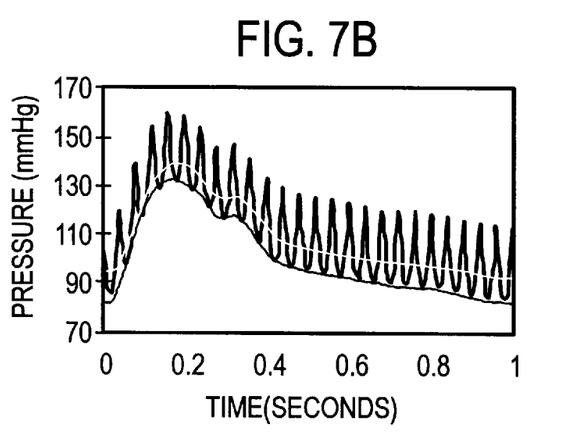
Figure 7C:
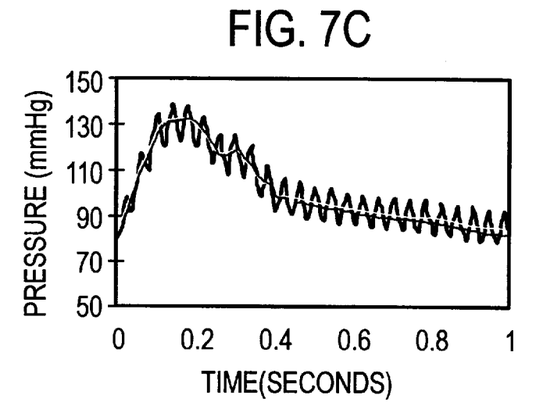

FIGS. 7A–7C depict the pressure signal output on line 27 by the pressure sensor 25 for the time period of one complete arterial pulse, for conditions of under compression, over compression, and optimal compression, respectively. It will be noted that the signals closely follow the actual arterial pressure waveform, which also is shown in the three drawings. It will be noted that a pressure oscillation due to the 25-Hz modulation signal is present in each of the depicted pressure signals.

In the under compression condition (FIG. 7A), the 25-Hz component of the pressure signal is skewed with its positive lobes significantly smaller than its negative lobes. Conversely, in the over compression condition (FIG. 7B), the 25-Hz component of the pressure signal is skewed with its negative lobes significantly smaller than its positive lobes. In the optimal compression condition (FIG. 7C), the 25-Hz component has positive and negative lobes of substantially the same amplitude. In addition, the total ac amplitude of the 25-Hz component of the pressure signal is smaller than it is when either under compressed or over compressed. This, of course, naturally follows from the shape of the sigmoid curve of FIG. 3; the incremental pressure will vary the least in response to an incremental artery diameter change at the point where the curve is steepest, i.e., where the artery's transmural pressure is zero.

The blood pressure monitoring apparatus of FIG. 6 implements a different technique from that of the apparatus of FIG. 2 to maintain the artery 21 at its optimum amount of compression. In the FIG. 6 apparatus, the analyzer 53 of the volume controller 35 examines the relative amplitudes of the positive and negative lobes of the 25-Hz component of the pressure signal, which is provided to the analyzer on line from the 25-Hz bandpass filter 49. If the negative lobes are determined to be larger than the positive lobes, then it is deduced that the artery is under compressed and an appropriate error signal is coupled to the summer 45 and, in turn, the liquid source 37. Conversely, an error signal having the opposite sense is produced if the positive lobes are determined to be larger than the negative lobes, in which case it is deduced that the artery is over compressed.

As mentioned above, the pressure signal produced by the pressure sensor 25 closely follows the actual arterial pressure waveform. This benefit is due primarily to the servo control of the flexible diaphragm 15 of the sensor assembly 11 such that the effective diameter of the artery 21 remains substantially fixed throughout each arterial pulse, as well as to the effective low compliance of the liquid within the chamber 23. The schematic diagram of FIG. 8 will help to provide an understanding of this phenomenon.

Figure 8:
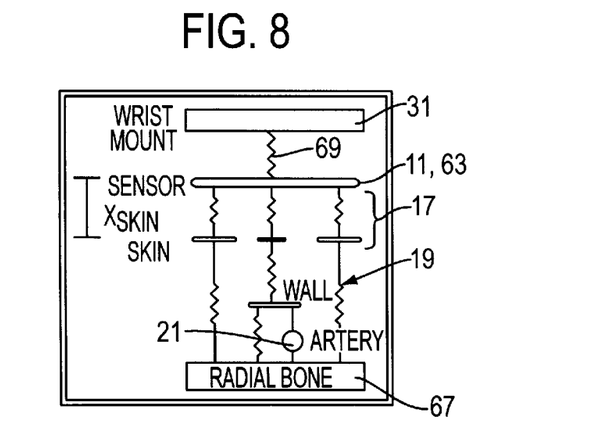
FIG. 8 is a schematic diagram of a model of the subject's wrist, with the pressure sensor assembly of FIG. 1 disposed adjacent to it. The diagram schematic representations of the wrist's radial bone, radial artery, skin, and underlying tissue.

The schematic diagram of FIG. 8 includes a simple, one-dimensional spring model of the subject's wrist 13, including its radial artery 21, radial bone 67, and skin 17, as well as the tissue 19 located above and adjacent to the radial artery. Also included in the schematic diagram is a simple, one-dimensional spring model of the sensor assembly 11, including its wrist strap 31. The radial bone advantageously serves as a fairly rigid backing for the radial artery, but the artery wall and the tissue above and adjacent to the radial artery are modeled as a plurality of resilient springs. The coupling between the wrist strap and the base 29 of the sensor assembly also is modeled as a spring.

It will be appreciated that if the flexible diaphragm 15 is servo controlled so as to minimize any variation in the effective diameter of the artery 21, then the attenuating effects of the various springs that represent the wall of the artery, the skin 17, and adjacent wrist tissue 19 is effectively eliminated. The only remaining element having an attenuating effect is the spring 69 that models the coupling between the base 29 of the sensor assembly 11 and the wrist strap 31. This dramatically improves the coupling of the arterial waveform to the pressure sensor 25, whereby a substantially improved pressure signal can be produced.

Figure 9:
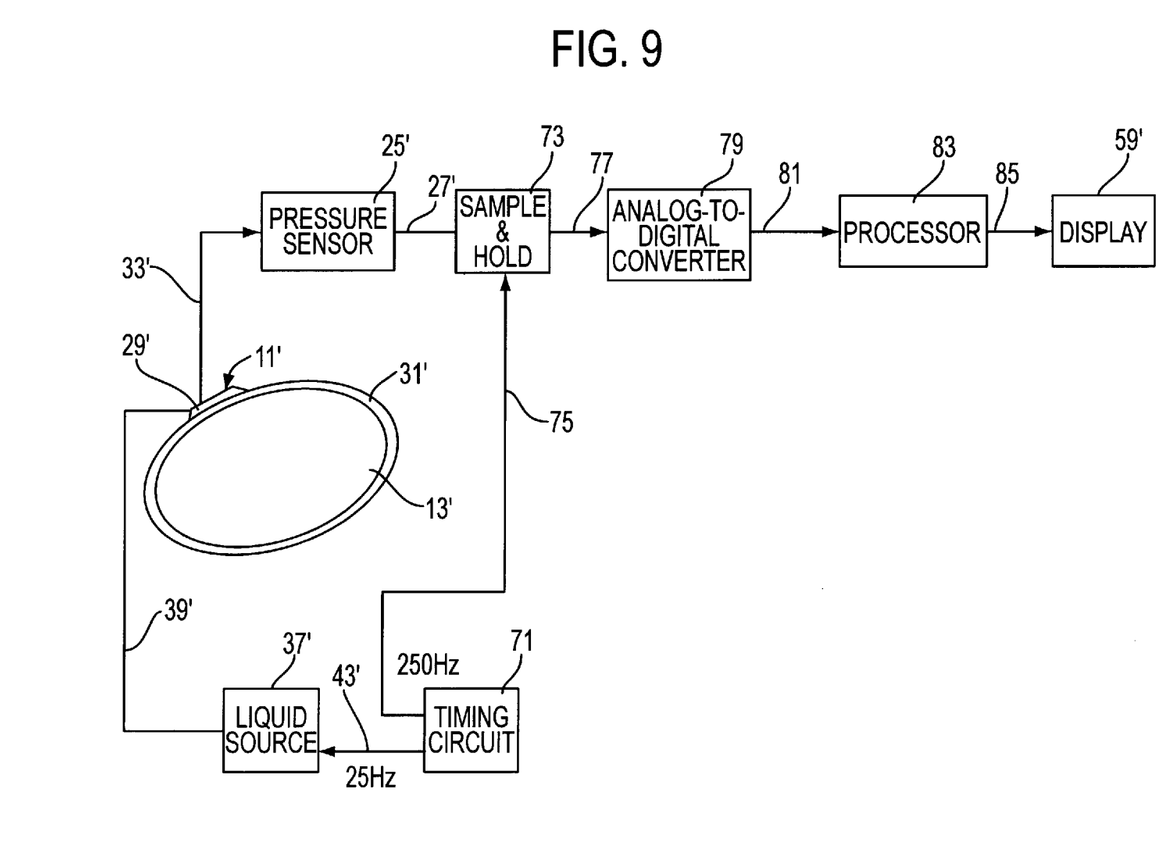
FIG. 9 is a block diagram of a third embodiment of a blood pressure monitoring apparatus in accordance with the invention, which incorporates the pressure sensor assembly of FIG. 1 and provides an accurate depiction of a subject's arterial pressure waveform within as little as a single heartbeat.

In another independent feature of the invention, an accurate depiction of the subject's blood pressure waveform, and an accurate measurement of arterial pulse pressure amplitude, can be produced within as little as a single heartbeat using a monitoring apparatus as depicted in FIG. 9, which implements a special control and monitoring algorithm. Some elements of the apparatus of FIG. 9 correspond to elements of the apparatus of FIG. 2, and these elements are identified by the same reference numerals, but with an added prime (') symbol. Although the FIG. 9 apparatus is depicted as an open-loop system, it alternatively could be implemented as a closed-loop system incorporating additional elements corresponding to those of the apparatus of FIG. 2 and/or FIG. 6.

More particularly, and with reference to FIG. 9, a liquid source 37' is connected via a conduit 39' to a chamber defined in a pressure sensor assembly 11'. The sensor assembly includes a plastic base 29' and a flexible diaphragm that cooperate to form the chamber, and this assembly is configured to be held in compressive engagement with a subject's wrist 13' by a wrist strap 31'. Actually, because the pressure waveform ordinarily can be produced within merely a few seconds, the wrist strap can be eliminated and the apparatus operated simply by pressing the diaphragm manually against the subject's wrist.

A clock circuit 71 supplies a 25-Hz sine wave signal on line 43' to the liquid source 37', to cause to liquid to be supplied to, and drawn from, the chamber of the pressure sensor assembly 11' in a sinusoidal fashion. If the assembly is being urged against the subject's wrist 13' such that the arterial wall is partially compressed, this volume modulation ordinarily will cause a corresponding sinusoidal pressure variation about a mean pressure within the chamber. This pressure variation is detected by a pressure sensor 25', which is connected to the chamber via a conduit 33', to produce an analog pressure signal output on line 27'.

Figure 10A:
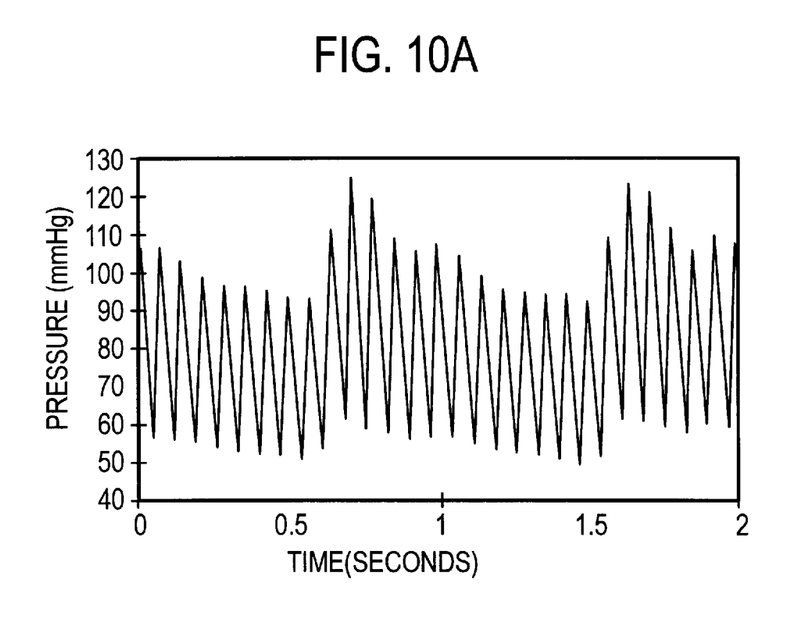
FIG. 10A is a graph of an exemplary pressure signal produced by the blood pressure monitoring apparatus of FIG. 9, incorporating both a sinusoidal modulation component and a subject heartbeat component.

One representative waveform for the analog pressure signal on line 27' is depicted in FIG. 10A, which corresponds to a situation in which the pressure sensor assembly 11' is being urged against the subject's wrist 13' with a mean pressure of about 80 mmHg. It will be noted that the pressure signal includes not only a 25-Hz modulation component, but also a heartbeat component. The apparatus of FIG. 9 functions effectively to demodulate this waveform and thereby to produce an accurate representation of the subject's actual blood pressure waveform.

The apparatus of FIG. 9 achieves this demodulation by sampling the analog pressure signal on line 27' at a sample rate that is an integral multiple of the 25-Hz modulation frequency. At a sample rate of 250 Hz, for example, ten samples would be provided for each modulation cycle. Since the first sample of each successive modulation cycle is produced while the 25-Hz modulation component is at the same level, it follows that these first samples can be associated together to produce a depiction of the subject's variable arterial pressure for that particular level. The same is true for each of ten separate sets of samples. Thus, ten separate pressure waveforms can be generated, each representing a different nominal arterial compression.

Figure 10B:
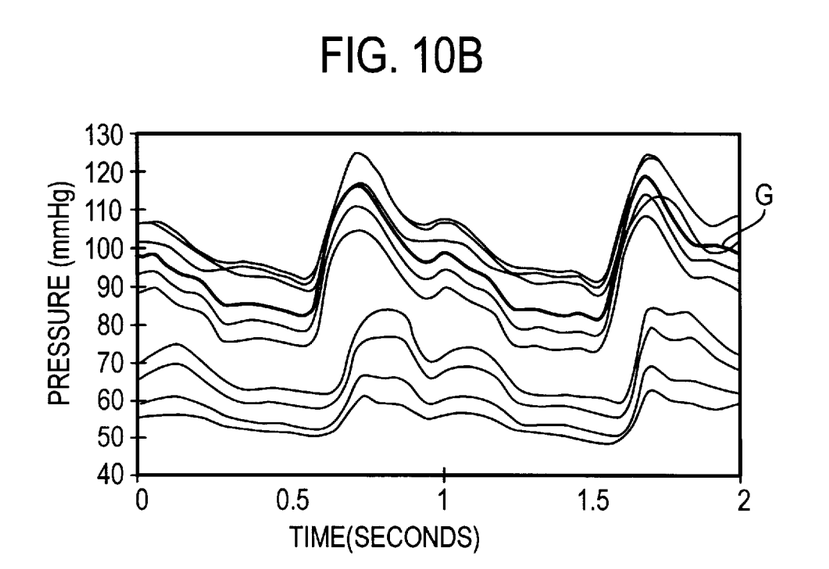
FIG. 10B is a graph of ten reconstructed pressure waveforms reconstructed from the exemplary pressure signal of FIG. 10A by the blood pressure monitoring apparatus of FIG. 9.

Exemplary versions of these ten separate pressure waveforms are depicted in FIG. 10B. It will be noted that the waveform having the lowest magnitude represents the pressure samples that are made when the 25-Hz modulation waveform is at its lowest value, and that the waveform having the highest magnitude represents the pressure samples that are made when the 25-Hz modulation waveform is at its highest value. The particular one of the ten waveforms that provides the greatest difference between the systolic and diastolic values is deemed to be produced when the subject's artery is compressed by the particular amount that provides optimal coupling to the pressure sensor assembly 11'. In the exemplary case depicted in FIG. 10B, this particular waveform is depicted by the bold reference line G.

It will be appreciated that the particular one of the ten waveforms that is considered optimal will vary depending on the nominal pressure applied by the pressure sensor assembly 11' to the subject's wrist 13'. If the nominal pressure is relatively low, then the optimal waveform will likely be one of the higher-level waveforms, which are produced when the 25-Hz modulation signal is at or near its positive peak. On the other hand, if the nominal pressure is relatively high, then the optimal waveform will likely be one of the lower-level waveforms, which are produced when the 25-Hz modulation signal is at or near its negative peak.

With reference again to FIG. 9, the successive samples of the analog pressure signal on line 27' are produced by a sample-and-hold circuit 73, under the control of a 250-Hz clock signal supplied on line 75 from the clock circuit 71. The resulting samples are supplied on line 77 to an analog-to-digital converter 79, which produces a succession of digital words that are coupled on lines 81 to a suitable processor 83. The processor associates together the successive samples, as discussed above, to produce the ten separate waveforms, and it ascertains the particular waveform that corresponds to the optimum level of nominal artery compression. This particular waveform is then coupled via line 85 to a display 59'.

It will be appreciated that results similar to those provided by the apparatus of FIG. 9 alternatively could be provided by substituting a tonometric sensor assembly for the depicted fluidically coupled sensor assembly. The important feature to be retained is that the position of the sensor assembly relative to the subject's artery be modulated and that the resulting pressure signal be sampled at a rate that is an integral multiple of the modulation frequency.

It should be appreciated from the foregoing description that the present invention provides an improved apparatus for monitoring a subject's blood pressure, non-invasively, in which a flexible diaphragm is compressed against tissue overlying an artery with sufficient force to compress the artery by an amount that optimally couples pressure waveforms within the artery. In addition, the amount of liquid contained within a chamber located behind the diaphragm is servo controlled, to compensate for pressure variations due to arterial pulses. This minimizes variations in the artery's effective diameter, whereby the pressure within the liquid-filled chamber is made to closely follow the actual arterial pulse waveform.

Although the invention has been described in detail with reference only to the preferred embodiments, those skilled in the art will appreciate that various modifications can be made without departing from the invention. Accordingly, the invention is defined only by the following claims.

We claim:

1. Apparatus for non-invasively monitoring the pressure within a subject's blood vessel, comprising:

a pressure sensor assembly that produces a pressure signal indicative of the pressure applied against it;

a coupling device configured to urge the pressure sensor assembly into compressive engagement with tissue overlying a subject's blood vessel, to compress the vessel and ensure that pressure variations within the vessel are coupled through the tissue to the pressure sensor assembly; and a controller that controllably modulates the position of the pressure sensor assembly relative to the subject's blood vessel and that monitors the resulting effect on the pressure signal, to produce a control signal that controllably positions the pressure sensor assembly relative to the subject's blood vessel such that the vessel is compressed by a prescribed amount.

2. Apparatus as defined in claim 1, wherein the coupling device urges the pressure sensor assembly to a position that partially compresses the blood vessel and provides a mean transmural vessel pressure of substantially zero.

3. Apparatus as defined in claim 1, wherein the pressure sensor assembly includes:

a base having an open cavity;

a flexible diaphragm extending across the open cavity of the base to define a closed, fluid-filled chamber; and a sensor device that senses the pressure of the fluid within the closed chamber and produces the corresponding pressure signal.

4. Apparatus as defined in claim 3, wherein the controller is a fluid volume controller configured to controllably supply a fluid to and from the closed chamber, to vary the position of the flexible diaphragm relative to the tissue overlying the subject's blood vessel, such that the blood vessel is compressed by the prescribed amount.

5. Apparatus as defined in claim 4, wherein:

the fluid volume controller is configured to modulate the volume of fluid within the closed chamber and to monitor the resulting effect on the pressure signal, and the control signal produced by the fluid volume controller regulates the amount of fluid within the chamber.

6. Apparatus as defined in claim 5, wherein:

the fluid volume controller is configured to modulate the volume of fluid within the closed chamber at a substantially uniform ac amplitude; and the fluid volume controller includes a device that compares the ac amplitude of the pressure signal during systole with the ac amplitude of the pressure signal during diastole and that produces the control signal in accordance with the comparison.

7. Apparatus as defined in claim 5, wherein:

the fluid volume controller is configured to modulate the volume of fluid within the closed chamber substantially sinusoidally; and the fluid volume controller includes a device that compares the ac amplitude of the pressure signal during positive portions of the fluid volume modulation with the ac amplitude of the pressure signal during negative portions of the fluid volume modulation and that produces the control signal in accordance with the comparison.

8. Apparatus as defined in claim 4, wherein:

the fluid is a liquid; and the subject's blood vessel is a peripheral artery.

9. Apparatus as defined in claim 1, wherein:

the subject's blood vessel is a radial artery; and the pressure sensor assembly is sized to extend only over the portion of the subject's wrist that overlies the radial artery.

10. Apparatus as defined in claim 1, wherein the controller includes:

a vessel geometry sensor that produces a vessel geometry signal indicative of the actual geometry of the subject's blood vessel;

an error signal generator that generates an error signal indicative of any difference between the actual geometry of the blood vessel and a prescribed geometry of the vessel; and a summer, responsive to the vessel geometry signal and the error signal, that produces the control signal.

11. Apparatus as defined in claim 10, wherein:

the pressure sensor assembly includes a base having an open cavity, a flexible diaphragm extending across the open cavity of the base to define a closed, fluid-filled chamber, and a sensor device that senses the pressure of the fluid within the closed chamber and produces the corresponding pressure signal; and the vessel geometry sensor is a diaphragm position sensor and the vessel geometry signal is indicative of the actual position of the flexible diaphragm relative to the base.

12. Apparatus as defined in claim 10, wherein the error signal generator includes:

an oscillator that produces a modulation signal that is supplied to the summer, for incorporation into the control signal, to cause the controller to modulate the actual position of the pressure sensor assembly relative to a mean position; and an analyzer, responsive to the pressure signal, for sensing any deviation of the pressure sensor assembly's actual position from the pressure sensor assembly's prescribed position and to produce the error signal.

13. Apparatus as defined in claim 12, wherein:

the modulation signal includes a succession of alternating positive and negative lobes; and the analyzer is configured to compare the effect that positive lobes of the modulation signal have on pressure signal amplitude with the effect that negative lobes of the modulation signal have on pressure signal amplitude, to sense any deviation of the pressure sensor assembly's actual position from the pressure sensor assembly's prescribed position and to produce the error signal.

14. Apparatus as defined in claim 12, wherein:

the modulation signal has a substantially uniform ac amplitude; and the analyzer is configured to compare the ac amplitude of the pressure signal during a first stage of the subject's heartbeat with the ac amplitude of the pressure signal during a second stage of the subject's heartbeat, to sense any deviation of the pressure sensor assembly's actual position from the pressure sensor assembly's prescribed position and to produce the error signal.

15. Apparatus as defined in claim 12, wherein:

the subject's blood vessel is an artery; and the modulation signal is a sine wave having a frequency substantially greater than the subject's expected heartbeat frequency.

16. Apparatus as defined in claim 1, wherein:

the controller is configured to modulate the position of the pressure sensor assembly relative to the subject's blood vessel at a substantially uniform ac amplitude; and the controller includes a device that compares the ac amplitude of the pressure signal during systole with the ac amplitude of the pressure signal during diastole, to produce the control signal in accordance with the comparison.

17. Apparatus as defined in claim 1, wherein:

the controller is configured to modulate the position of the pressure sensor assembly relative to the subject's blood vessel substantially sinusoidally; and the controller includes a device that compares the ac amplitude of the pressure signal during positive portions of the vessel modulation with the ac amplitude of the pressure signal during negative portions of the vessel modulation, to produce the control signal in accordance with the comparison.

18. Apparatus for non-invasively monitoring the pressure within a subject's blood vessel, comprising:

a base having an open cavity;

a flexible diaphragm extending across the open cavity of the base to define a closed, fluid-filled chamber;

a coupling device configured to urge the diaphragm into compressive engagement with tissue overlying a subject's blood vessel, to compress the vessel and ensure that pressure variations within the vessel are coupled through the tissue to the diaphragm;

a fluid volume controller that supplies a fluid to and from the closed chamber in accordance with a modulation signal, such that the flexible diaphragm oscillates about an actual mean position;

a pressure sensor that senses the pressure of the fluid within the closed chamber and produces a corresponding pressure signal;

an analyzer, responsive to the pressure signal, for sensing any deviation of the flexible diaphragm's actual position from a prescribed position and to produce a corresponding error signal that is coupled to the fluid volume controller, to cause the volume controller to supply fluid to or from the closed chamber, to move the flexible diaphragm toward the prescribed position;

a filter that filters the pressure signal to produce a filtered pressure signal indicative of the pressure within the subject's blood vessel.

19. Apparatus as defined in claim 18, wherein:

the apparatus further includes a diaphragm position sensor that produces a diaphragm position signal indicative of the flexible diaphragm's actual position relative to the base; and the fluid volume controller is configured to supply the fluid to and from the closed chamber in accordance with the diaphragm position signal, such that the position of the portion of the flexible diaphragm overlying the subject's blood vessel remains substantially fixed despite pressure variations within the blood vessel.

20. Apparatus as defined in claim 18, wherein:

the modulation signal has a substantially uniform ac amplitude; and the analyzer is configured to compare the amplitude of the pressure signal during a first stage of the subject's heartbeat with the amplitude of the pressure signal during a second stage of the subject's heartbeat, to sense any deviation of the flexible diaphragm's actual position from the flexible diaphragm's prescribed position and to produce the error signal.

21. Apparatus as defined in claim 18, wherein:

the modulation signal includes a succession of alternating positive and negative lobes; and the analyzer is configured to compare the effect that positive lobes of the modulation signal have on pressure signal amplitude with the effect that negative lobes of the modulation signal have on pressure signal amplitude, to sense any deviation of the flexible diaphragm's actual mean position from the flexible diaphragm's prescribed mean position and to produce the error signal.

22. Apparatus for non-invasively monitoring the pressure within a subject's blood vessel, comprising:

a base having an open cavity;

a flexible diaphragm extending across the open cavity of the base to define a fluid-filled chamber;

a coupling device configured to urge the diaphragm into compressive engagement with tissue overlying a subject's blood vessel, to compress the vessel and ensure that pressure variations within the vessel are coupled through the tissue to the diaphragm;

a first control system that supplies fluid to and from the fluid-filled chamber such that the portion of the flexible diaphragm overlying the subject's blood vessel has a prescribed position that optimally compresses the blood vessel;

a second control system that supplies fluid to and from the fluid-filled chamber so as to servo control the position of the flexible diaphragm and maintain the diaphragm in its prescribed position despite pressure variations within the subject's blood vessel; and a pressure sensor that senses the pressure of the fluid within the fluid-filled chamber and produces a corresponding pressure signal indicative of the pressure within the subject's blood vessel.

23. An apparatus for non-invasively monitoring the pressure within a subject's blood vessel, comprising:

a base having an open cavity;

a flexible diaphragm extending across the open cavity of the base to define a closed, fluid-filled chamber;

a coupling device configured to urge the diaphragm into compressive engagement with tissue overlying a subject's blood vessel, to compress the vessel and ensure that pressure variations within the vessel are coupled through the tissue to provide a variable force against the diaphragm;

a fluid volume controller that controllably supplies fluid to and from the closed chamber, to substantially balance the variable force applied to the diaphragm by any pressure variations in the subject's blood vessel;

a sensor that senses the pressure of the fluid within the closed chamber and produces a corresponding pressure signal indicative of the pressure within the subject's blood vessel; and a filter that filters the pressure signal to produce a filtered pressure signal indicative of the pressure within the subject's blood vessel;

wherein the fluid volume controller includes a fluid source that applies fluid to and from the closed chamber in accordance with a modulation signal, such that the flexible diaphragm oscillates about an actual position, wherein this oscillation induces a corresponding oscillation in the pressure signal produced by the sensor, and an analyzer, responsive to the pressure signal, for sensing any deviation of the flexible diaphragm's actual position from a prescribed position and to produce a corresponding error signal that is coupled to the fluid source, to cause the fluid source to supply fluid to or from the closed chamber to move the diaphragm toward the prescribed position.

24. Apparatus as defined in claim 23, wherein:

the apparatus further includes a diaphragm position sensor that produces a diaphragm position signal indicative of the flexible diaphragm's actual position relative to the base; and the fluid source is configured to supply the fluid to and from the closed chamber in accordance with the diaphragm position signal, such that the position of the portion of the flexible diaphragm overlying the subject's blood vessel remains substantially fixed despite pressure variances within the blood vessel.

25. Apparatus as defined in claim 23, wherein:

the modulation signal has a substantially uniform ac amplitude; and the analyzer is configured to compare the amplitude of the pressure signal during a first stage of the subject's heartbeat with the amplitude of the pressure signal during a second stage of the subject's heartbeat, to sense any deviation of the flexible diaphragm's actual position from the flexible diaphragm's prescribed position and to produce the error signal.

26. Apparatus as defined in claim 23, wherein:

the modulation signal includes a succession of alternating positive and negative lobes; and the analyzer is configured to compare the effect that positive lobes of the modulation signal have on pressure signal amplitude with the effect that negative lobes of the modulation signal have on pressure signal amplitude, to sense any deviation of the flexible diaphragm's actual position from the flexible diaphragm's prescribed position and to produce the error signal.

27. Apparatus as defined in claim 23, wherein:

the subject's blood vessel is an artery; and the modulation signal is a sine wave having a frequency substantially greater than the subject's expected heartbeat frequency.

28. Apparatus as defined in claim 23, wherein:

the fluid is a liquid; and the subject's blood vessel is a peripheral artery.

29. Apparatus as defined in claim 28, wherein:

the peripheral artery is a radial artery; and the diaphragm is sized to extend only over the portion of the subject's wrist that overlies the radial artery.

30. An apparatus for non-invasively monitoring the pressure within a subject's blood vessel, comprising:

a base having an open cavity;

a flexible diaphragm extending across the open cavity of the base to define a closed, fluid-filled chamber;

a coupling device configured to urge the diaphragm into compressive engagement with tissue overlying a subject's blood vessel, to compress the vessel and ensure that pressure variations within the vessel are coupled through the tissue to provide a variable force against the diaphragm;

a fluid volume controller that controllably supplies fluid to and from the closed chamber, to substantially balance the variable force applied to the diaphragm by any pressure variations in the subject's blood vessel, wherein the fluid volume controller is configured to maintain the subject's blood vessel optimally compressed continuously, without the need for separate calibration; and a sensor that senses the pressure of the fluid within the closed chamber and produces a corresponding pressure signal indicative of the pressure within the subject's blood vessel.

31. A method for non-invasively monitoring the pressure within a subject's blood vessel, comprising:

providing a pressure sensor assembly that produces a pressure signal indicative of the pressure applied against it;

urging the pressure sensor assembly into compressive engagement with tissue overlying a subject's blood vessel, to compress the vessel and ensure that pressure variations within the vessel are coupled through the tissue to the pressure sensor assembly; and controllably modulating the position of the pressure sensor assembly relative to the subject's blood vessel and monitoring the resulting effect on the pressure signal, to produce a control signal that controllably positions the pressure sensor assembly relative to the subject's blood vessel such that the vessel is compressed by a prescribed amount.

32. A method as defined in claim 31, wherein urging includes the pressure sensor assembly to a position that partially compresses the blood vessel and provides a mean transmural vessel pressure of substantially zero.

33. A method as defined in claim 31, wherein:

the pressure sensor assembly includes
- a base having an open cavity,
- a flexible diaphragm extending across the open cavity of the base to define a closed, fluid-filled chamber, and
- a sensor device that senses the pressure of the fluid within the closed chamber and produces the corresponding pressure signal; and controlling includes controllably supplying fluid to and from the closed chamber, to vary the position of the flexible diaphragm relative to the tissue overlying the subject's blood vessel, such that the blood vessel is compressed by the prescribed amount.

34. A method as defined in claim 33, wherein:

controlling includes modulating the volume of fluid within the closed chamber and monitoring the resulting effect on the pressure signal, and the control signal regulates the mean amount of fluid within the chamber.

35. A method as defined in claim 34, wherein:

controlling includes modulating the volume of fluid within the closed chamber at a substantially uniform ac amplitude; and controlling further includes comparing the ac amplitude of the pressure signal during systole with the ac amplitude of the pressure signal during diastole and producing the control signal in accordance with the comparison.

36. A method as defined in claim 34, wherein:

controlling includes modulating the volume of fluid within the closed chamber substantially sinusoidally; and controlling further includes comparing the ac amplitude of the pressure signal during positive portions of the fluid volume modulation with the ac amplitude of the pressure signal during negative portions of the fluid volume modulation and producing the control signal in accordance with the comparison.

37. A method as defined in claim 31, wherein controlling includes:

sensing vessel geometry and producing a vessel geometry signal indicative of the actual geometry of the subject's blood vessel;

generating an error signal indicative of any difference between the actual geometry of the blood vessel and a prescribed geometry of the vessel; and producing the control signal based on the vessel geometry signal and the error signal.

38. A method as defined in claim 37, wherein:

the pressure sensor assembly includes
- a base having an open cavity,
- a flexible diaphragm extending across the open cavity of the base to define a closed, fluid-filled chamber, and
- a sensor device that senses the pressure of the fluid within the closed chamber and produces the corresponding pressure signal; and sensing vessel geometry sensor includes sensing the position of the diaphragm sensor, such that the vessel geometry signal is indicative of the actual position of the flexible diaphragm relative to the base.

39. A method as defined in claim 37, wherein generating includes:

modulating the actual position of the pressure sensor assembly relative to a mean position, the modulation being in accordance with a modulation signal; and monitoring the modulation signal and the pressure signal, to sense any deviation of the pressure sensor assembly's actual position from the pressure sensor assembly's prescribed position and to produce the error signal.

40. A method as defined in claim 39, wherein:

the modulation signal includes a succession of alternating positive and negative lobes; and monitoring includes comparing the effect that positive lobes of the modulation signal have on pressure signal amplitude with the effect that negative lobes of the modulation signal have on pressure signal amplitude, and sensing any deviation of the pressure sensor assembly's actual position from the pressure sensor assembly's prescribed position, to produce the error signal.

41. A method as defined in claim 39, wherein:

the modulation signal has a substantially uniform ac amplitude; and monitoring includes comparing the ac amplitude of the pressure signal during a first stage of the subject's heartbeat with the ac amplitude of the pressure signal during a second stage of the subject's heartbeat, and sensing any deviation of the pressure sensor assembly's actual position from the pressure sensor assembly's prescribed position, to produce the error signal.

42. A method as defined in claim 31, wherein:

controlling includes modulating the position of the pressure sensor assembly relative to the subject's blood vessel at a substantially uniform ac amplitude; and controlling further includes comparing the ac amplitude of the pressure signal during systole with the ac amplitude of the pressure signal during diastole, and producing the control signal in accordance with the comparison.

43. A method as defined in claim 31, wherein:

controlling includes modulating the position of the pressure sensor assembly relative to the subject's blood vessel substantially sinusoidally; and controlling further includes comparing the ac amplitude of the pressure signal during positive portions of the vessel modulation with the ac amplitude of the pressure signal during negative portions of the vessel modulation, and producing the control signal in accordance with the comparison.

* * * * *